United States Patent [19]

Tsujii et al.

[11] Patent Number: 5,043,354
[45] Date of Patent: Aug. 27, 1991

[54] PHARMACEUTICALLY USEFUL 5-HYDROXY-2,3-DIHYDRO-BENZOFURANS AND 5-HYDROXY-BENZOFURANS

[75] Inventors: Eisaku Tsujii; Yasuhisa Tsurumi; Masanori Okamoto; Masakuni Okuhara; Teruo Oku; Masashi Hashimoto, all of Tsukuba, Japan

[73] Assignee: Fujisawa Pharmaceutical Co., Ltd., Osaka, Japan

[21] Appl. No.: 520,061

[22] Filed: May 3, 1990

[30] Foreign Application Priority Data

May 15, 1989 [GB] United Kingdom ............... 8911073

[51] Int. Cl.$^5$ ............... C07D 307/79; C07D 307/80; A61K 31/34
[52] U.S. Cl. .................... 514/469; 435/126; 435/254; 549/462; 549/471
[58] Field of Search ............ 549/462, 471, 470; 514/469

[56] References Cited

U.S. PATENT DOCUMENTS 4,966,907  10/1990  Caldwell et al. ............... 549/462

FOREIGN PATENT DOCUMENTS 2193211  2/1988  United Kingdom .

OTHER PUBLICATIONS

Chem. Abstracts-vol. 75, 137491d (1971); Alertsen et al., Acta Chem. Scand. vol. 25(5), pp. 1919-1920 (1971).

Primary Examiner—Bernard Dentz
Attorney, Agent, or Firm—Oblon, Spivak, McClelland, Maier & Neustadt

[57] ABSTRACT

A compound of the formula:

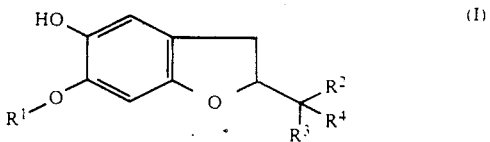

wherein $R^1$, $R^2$ and $R^3$ are each lower alkyl, $R^4$ is hydrogen or hydroxy, and a heavy solid line means a double bond when $R^4$ is hydrogen and a single bond when $R^4$ is hydroxy is useful in the treatment of diseases caused by reactive oxygen species and organic radicals.

4 Claims, No Drawings

PHARMACEUTICALLY USEFUL 5-HYDROXY-2,3-DIHYDRO-BENZOFURANS AND 5-HYDROXY-BENZOFURANS

This invention relates to new benzofuran derivatives and pharmaceutically acceptable salts thereof.

More particularly, it relates to new benzofuran derivatives and pharmaceutically acceptable salts thereof which have an activity to scavenge reactive oxygen species and organic radicals, to a process for the preparation thereof, to a pharmaceutical composition comprising the same and to a method for the treatment of the diseases caused by reactive oxygen species and organic radicals in human beings or animals, and more particularly to method for the treatment of ischemic heart diseases (e.g. arrhythmia, coronary vasospasm, necrosis of cardiac tissue, myocardial infarction, etc.), ischemic cerebral diseases (e.g. cerebral infarction, dementia, senile dementia, etc.), disorders of the liver, pancreas and kidney and the like.

One object of this invention is to provide new and useful benzofuran derivatives and pharmaceutically acceptable salts thereof which possess an activity to scavenge reactive oxygen species and organic radicals.

Another object of this invention is to provide processes for the preparation of the said benzofuran derivatives and salts thereof.

A further object of this invention is to provide a pharmaceutical composition comprising, as an active ingredient, the said benzofuran derivatives and pharmaceutically acceptable salts thereof.

Still further object of this invention is to provide a therapeutic method for the treatment of the diseases caused by reactive oxygen species and organic radicals in human beings or animals, and more particularly of ischemic heart diseases (e.g. arrhythmia, coronary vasospasm, necrosis of cardiac tissue, myocardial infarction, etc.), ischemic cerebral diseases (e.g. cerebral infarction, dementia, senile dementia, etc.), disorders of the liver, pancrea and kidney and the like, using the said benzofuran derivatives and pharmaceutically acceptable salts thereof.

Some compounds having an activity to scavenge reactive oxygen species and organic radicals have been known as described, for example, in EP Patent Application Nos. 173,331, 202,589 and 273,647.

With respect to the present invention, it is to be noted that this invention is originated from and based on the first and new discovery of a new certain specific compound, FR-901242 substance. In more detail, the FR-901242 substance was firstly and newly isolated in pure form culture broths obtained by fermentation of new species belonging to the hyphomycete genus Paecilomyces.

And, as a result of an extensive study for elucidation of a chemical structure of the FR-901242 substance, the inventors of this invention have succeeded in determining the chemical structure thereof and in producing its racemic compound which possesses the similar activity to the FR-901242 substance.

The new benzofuran derivatives of this invention are represented by the following formula:

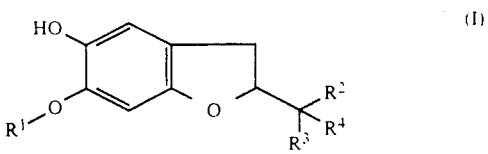

wherein
$R^1$, $R^2$ and $R^3$ are each lower alkyl,
$R^4$ is hydrogen or hydroxy, and a heavy solid line means a single or a double bond,
provided that when $R^4$ is hydrogen, then a heavy solid line means a double bond.
when $R^4$ is hydroxy, then a heavy solid line means a single bond, and
pharmaceutically acceptable salts thereof.

Among the object compound (I), the optically active specific compound (I) wherein $R^1$, $R^2$ and $R^3$ are each methyl, $R^4$ is hydroxy and a heavy solid line means a single bond, which is named as the FR-901242 substance was found to be produced by fermentation.

With respect to the benzofuran derivatives (I) of this invention, it is to be understood that there may be optical isomers due to asymmetric carbon atom(s), and such isomers are also included within the scope of this invention.

The object compound (I) or its salt can be prepared by the following processes.

[I] Fermentation Process:

Species belonging to the hyphomycete genus Paecilomyces ——Fermentation——> FR-901242 substance

[II] Synthetic Process:

(1) Process 1

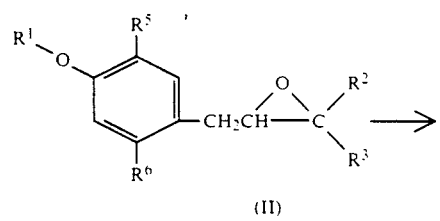

(2) Process 2

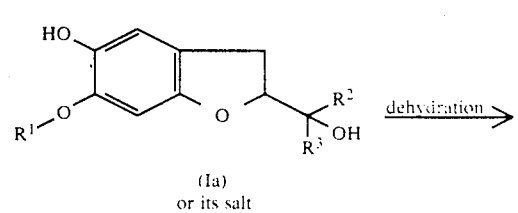

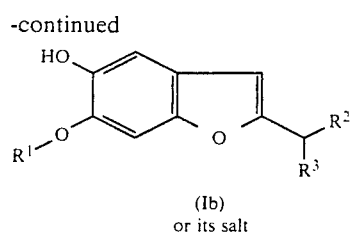

(Ib)
or its salt wherein $R^5$ and $R^6$ are each protected hydroxy, and $R^1$, $R^2$ and $R^3$ are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" is methyl, ethyl, propyl, isopropyl, butyl, pentyl, hexyl and the like, preferably one having 1 to 2 carbon atom(s), more preferably methyl.

Suitable hydroxy-protective group in the "protected hydroxy" may include acyl such as substituted or unsubstituted aliphatic acyl and substituted or unsubstituted aromatic acyl, which are derived from carboxylic, carbonic, sulfonic and carbamic acids; and the like.

The substituted or unsubstituted aliphatic acyl may include lower alkanoyl (e.g. formyl, acetyl, propionyl, butyryl, isobutyryl, valeryl, isovaleryl, pivaloyl, etc.), lower alkoxycarbonyl (e.g. methoxycarbonyl, ethoxycarbonyl, tert-butoxycarbonyl, etc.), lower alkanesulfonyl (e.g. methanesulfonyl, ethanesulfonyl, etc.), lower alkylcarbamoyl (e.g. methylcarbamoyl, ethylcarbamoyl, etc.), and the like.

The substituted or unsubstituted aromatic acyl may include aroyl (e.g. benzoyl, toluoyl, xyloyl, naphthoyl, etc.), nitro aroyl (e.g. nitrobenzoyl, dinitrobenzoyl, etc.), phenoxycarbonyl, arenesulfonyl (e.g. benzenesulfonyl, toluenesulfonyl, etc.), and the like.

Suitable pharmaceutically acceptable salts of the object compound (I) are conventional non-toxic salts and include an inorganic base salt such as an alkali metal salt [e.g. sodium salt, potassium salt, etc.], an alkaline earth metal salt [e.g. calcium salt, magnesium salt, etc.], and the like.

The processes for preparing the object compound (I) is explained in detail in the following.

[I] Fermentation Process

The FR-901242 substance of this invention can be produced by fermentation of FR-901242 substance-producing strain belonging to the hyphomycete genus Paecilomyces such as Paecilomyces sp. F-18826 in nutrient medium.

Particulars of the microorganism used for the production of the FR-901242 substance are explained in the following.

THE MICROORGANISM

This microorganism which can be used for the production of the FR-901242 substance is FR-901242 substance-producing strain belonging to the hyphomycete genus Paecilomyces, among which Paecilomyces sp. F-18826 has been newly isolated from a decayed leaf debris, collected at the foot of Mt. Yamizo, Ibaraki Prefecture, Japan.

This Paecilomyces sp. F-18826 strain has been deposited with the following International Depository Authority under the Budapest Treaty : Fermentation Research Institute of the Agency of Industrial Science and Technology.
Identification number : FERM BP-2322
Address : 1-3, Higashi 1 chome, Tsukuba-shi, Ibaraki-ken 305, Japan;

It is to be understood that the production of the novel FR-901242 substance is not limited to the use of the particular organism described herein, which is given for the illustrative purpose only. This invention also includes the use of any mutants which are capable of producing the FR-901242 substance including natural mutants as well as artificial mutants which can be produced from the described organism by conventional means such as irradiation of X-rays, ultra-violet radiation, treatment with N-methyl-N'-nitro-N-nitrosoguanidine, 2-aminopurine, and the like.

The Paecilomyces sp. F-18826 has the following morphological, cultural, biological and physiological characteristics.

[1] Morphological Characteristics

Morphological observations were made with light and electron microscopes on cultures grown at 25° C. for 14 days on corn meal agar. The conidiophores were macronematous, mononematous, hyaline, smooth, septate, and formed in penicillate-fashion. The stipes, aristing from vegetative hyphae, were 70–120(–160) μm long and 2.5–4.0 μm thick, with 4.0–6.0 μm thick at the base. The terminal verticils, penicillin, were biverticillate and consisted of 2–3 metulae with the whorls of 3–5 phialides. The metulae were cylindrical and 12–17(–23)×3–5 μm in size. The phialides were lageniform, 10–12(–15)×4–6 μm, with narrowing neck measuring 2.0–2.5 μm thick. The conidia were borne in basipetal chains, measuring 100–300 μm long. They were hyaline, smooth, one-celled, oval to fusiform and 6.0–9.5×2.5–4.5 μm. The vegetative hyphae were smooth, septate, hyaline and branched. The hyphal cells were irregular shapes and 1.5–3.0 μm thick. The chlamydospores were absent.

[2] Cultural Characteristics

The incubation was made at 25° C. for 14 days. The color descriptions were based on the Methuen Handbook of Colour (Kornerup, A. and J. H. Wanscher : Methuen Handbook of Colour, Third ed., Methuen, London, 1983). This organism grew rapidly on various culture media, and formed yellowish white to pale yellow or greyish yellow colonies. The strain F-18826 formed anamorph, consisting of penicillate conidiophres and conidial chains, on some media. The conidiogenesis was phialidic (enteroblastic). The strain did not produce teleomorph structures. Culture on malt extract agar grew rapidly, attaining 4.0–4.5 cm in diameter after two weeks at 25° C. This colony surface was plane, thin, powdery and pale yellow or white. The reverse was yellowish white. Conidial structures were observed at colony center. Colonies on potato dextrose agar grew more rapidly than on malt extract agar, attaining 5.0–5.5 cm in diameter under the same condition. The surface was plane, powdery, wrinkly at the center, pale yellow or white to organge white. The reverse was yellowish white to yellowish grey. Conidial structures were abunduntly produced. The results are shown in Table 1.

TABLE 1

| Medium | Cultural characteristics of the strain F-18826 |
|---|---|
| Malt extract agar (Blaskeslee 1915) | G: Rapidly, 4.0–4.5 cm<br>S: Circular, plane, thin, powdery, formed conidial structures at the center, pale yellow (4A3) or white<br>R: Yellowish white (3A2) |
| Potato dextrose agar (Difco 0013) | G: Spreading broadly, 5.0–5.5 cm<br>S: Circular, plane, powdery, wrinkly at the center, abunduntly formed conidial structures, pale yellow (4A3) or white to orange white (6A2)<br>R: Yellowish white (2A2) to yellowish grey (2B2) |
| Czapek's solution agar (Raper and Thom 1949) | G: Very restrictedly, 0–0.5 cm<br>S: Irregular, plane, formed no conidial structure, white<br>R: White |
| Sabouraud dextrose agar (Difco 0190) | G: Restrictedly, 2.0–2.5 cm<br>S: Circular, convex, formed no conidial structure, greyish yellow (4B3)<br>R: Orange (5B8) |
| Oatmeal agar (Difco 0552) | G: Rapidly, 4.5–5.0 cm<br>S: Circular, plane, powdery, wrinkly, abunduntly formed conidial structures, yellowish white (4A2) or white to reddish white (7A2) |
| Emerson Yp Ss agar (Difco 0739) | G: Rapidly, 4.0–4.5 cm<br>S: Circular, plane, powdery, wrinkly, abunduntly formed conidial structures, white to reddish white (8A2)<br>R: Pale Yellow (3–5A3) |
| Corn meal agar (Difco 0386) | G: Spreading broadly, 5.0–5.5 cm<br>S: Circular, plane, thin, formed conidial structures, yellow white (1A2) to white<br>R: Yellowish white (1A2) |

Abbreviation
G: growth, measuring colony size in diameter
S: colony surface
R: reverse

[3] Biological and Physiological Properties

The strain F-18826 was able to grow at the temperature range from 3° to 32° C. with the growth optimum at 22° to 26° C. These temperature data were determined on potato dextrose agar. This strain could grow at pH 4 to 8, and had a growth optimum at pH 5 to 7 in YM broth (Difco).

From above-mentioned characteristics, the strain F-18826 was considered to belong the hyphomycete genus Paecilomyces Bainier 1907 (1), (2), (3) Then, we named the producing strain to Paecilomyces sp. F-18826.

(1) Arx, J. A. von: The Genera of Fungi-Sporulating in Pure Culture (3rd ed.), 315 p., J. Cramer, Vaduz, 1947.
(2) Brown, A. H. S. and G. Smith : The genus Paecilomyces Bainier and its perfect stage Byssochlamys Westling., Trans. Br. mycol. Soc., 40, pp. 17–89, 1957.
(3) Samson, R. A. : Paecilomyces and some allied Hyphomycetes., Studios Mycol., 6, pp. 1–119, 1974.

PRODUCTION OF FR-901242 SUBSTANCE

The novel FR-901242 substance of this invention can be produced by culturing the FR-901242 substance-producing strain belonging to the hyphomycete genus Paecilomyces (e.g. Paecilomyces sp. F-18826, FERM BP-2322) in a nutrient medium.

In general, the FR-901242 substance can be produced by culturing the FR-901242 substance-producing strain in an aqueous nutrient medium containing sources of assimilable carbon and nitrogen, preferably aerobic conditions (e.g. shaking culture, submerged culture, etc.).

The preferred sources of carbon in the nutrient medium are carbohydrates such as glucose, sucrose, lactose, glycerin, starch, dextrin, and the like. Other sources which may be included are maltose, D-trehalose, inositol, inulin, salicin, and the like.

The preferred sources of nitrogen are yeast extract, polypeptone, gluten meal, cotton-seed flour, soybean meal, corn steep liquor, dried yeast, wheat germ, feather meal, peanut powder etc., as well as inorganic and organic nitrogen compounds such as ammonium salts (e.g. ammonium nitrate, ammonium sulfate, ammonium phosphate, etc.), urea, amino acid, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium dihydrogenphosphate, sodium or potassium chloride, sodium or potassium iodide, zinc salts, magnesium salts, copper salts, cobalt salt and the like. If necessary, especially when the culture medium foams seriously, a deforming agent, such as liquid paraffin, fatty oil, plant oil, mineral oil or silicone may be added.

As the conditions for the production of the FR-901242 substance in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-901242 substance. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of the FR-901242 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 30° C., preferably 22°–26° C., for a period of about 50 hours to 150 hours, which may be varied according to fermentation conditions and scales.

Thus produced FR-901242 substance can be recovered from the culture medium by conventional means which are commonly used for the recovery of other known biologically active substance. The FR-901242 substance produced is found in the cultured filtrate, and accordingly the FR-901242 substance can be isolated and purified from the filtrate, which are obtained by filtering or centrifuging the cultured broth, by a conventional method such as concentration under reduced pressure, lyophilization, extraction with a conventional solvent, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like.

PHYSICAL AND CHEMICAL PROPERTIES OF FR-901242 SUBSTANCE

The FR-901242 substance produced according to the aforementioned process possesses the following physical and chemical properties.

FR-901242 substance (1) Form and Color :
Colorless needles
(2) Molecular weight :
224 (Mass spectrometry)
(3) Elemental Analysis :
Calcd. for $C_{12}H_{16}O_4$; C: 64.27%, H: 7.19%,
Found ; C: 63.98%, H: 7.31%.
(4) Color Reaction:
Positive : ferric chloride reaction, iodine vapor reaction, cerium sulfate reaction and potassium permanganate reaction
Negative : ninhydrin reaction, Molish reaction and Ehrlich reaction
(5) Solubility :
Soluble : chloroform, diethyl ether, ethyl acetate, acetone, methanol and ethanol
Sparingly Soluble : hexane, water
(6) Melting Point :
134° C.
(7) Specific Rotation :
$[\alpha]20$ D: $-21.7°$ (C=1, CHCl$_3$)
(8) Ultraviolet Absorption Spectrum :
MeOH λmax: 303 nm (ε=8050)
(9) Infrared Absorption Spectrum :
ChCl$_3$
$\nu_{max}$:3550, 2980, 2930, 2850, 1630, 1500, 1460, 1445, 1385, 1358, 1328, 1240, 1180, 1158, 1098, 1005, 960, 945, 870, 820, 730 cm$^{-1}$
(10) $^{13}C$ Nuclear Magnetic Resonance Spectrum
δ(ppm, CDCl$_3$) 23.88 (q), 26.10 (q), 30.80 (t), 56.18 (q), 71.79 (s), 89.72 (d), 93.91 (d), 110.64 (d), 117.87 (s), 139.64 (s), 145.97 (s), 152.78 (s)
(11) $^1H$ Nuclear Magnetic Resonance Spectrum :
δ(ppm, CDCl$_3$) 1.20 (3H, s), 1.32 (3H, s), 2.09 (1H, br s), 3.07 (2H, m), 3.82 (3H, s), 4.57 (1H, t, J=8.1Hz), 5.34 (1H, s), 6.41 (1H, s), 6.73 (1H, s)
(12) Thin Layer Chromatography :

| Stationary phase | Developing Solvent | Rf value |
|---|---|---|
| Silica gel plate* | chloroform: methanol (30:1, V/V) | 0.42 |
|  | n-hexane: ethyl acetate (1:1, V/V) | 0.45 |

*silica gel plate. Kieselgel 60 F$_{254}$ (made by E. Merck)

(13) Property of the Substance :
neutral substance

From the above physical and chemical properties, the FR-901242 substance could be determined to have the following chemical structure.

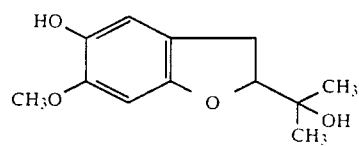

2,3-Dihydro-2-(1-hydroxy-1-methylethyl)-6-methoxy-5-benzofuranol

[II]Synthetic Process (1) Process 1
The compound (Ia) or its salt can be prepared by reacting the compound (II) with a base.

The suitable base may be an alkali metal (e.g. sodium, potassium, etc.), an alkaline earth metal (e.g. magnesium, calcium, etc.), the hydroxide or carbonate or bicarbonate thereof and the like.

This reaction is usually carried out in a conventional solvent such as alcohol (e.g. methanol, ethanol, etc.), acetone, dioxane, acetonitrile, chloroform, methylene chloride, tetrahydrofuran, N,N-dimethylformamide or any other organic solvent which does not adversely influence the reaction.

The reaction temperature is not critical, and the reaction is usually carried out under cooling to heating.

(2) Process 2
The compound (Ib) or its salt can be prepared by subjecting a compound (Ia) or its salt to dehydration reaction.

The suitable dehydrating agent used in this reaction may be acid [e.g. sulfuric acid, oxalic acid, phosphoric acid, p-toluenesulfonic acid, etc.], phosphorus compound [e.g. phosphorous pentoxide, phosphorus pentachloride, phosphorus oxychloride, etc.], thionyl chloride, acid anhydride [e.g. acetic anhydride, etc.], phosgene, arylsulfonyl chloride [e.g. benzenesulfonyl chloride, p-toluenesulfonyl chloride, etc.], methanesulfonyl chloride and the like.

The reaction is usually carried out in a conventional solvent such as acetonitrile, chloroform, methylene chloride, benzene, N,N-dimethylformamide, pyridine or any other organic solvent which does not adversely influence the reaction.

Additionally, in case that the above-mentioned dehydrating agents are in liquid, they can also be used as a solvent.

The reaction temperature is not critical and the reaction is usually carried out at ambient temperature, under warming or heating.

Pharmaceutically acceptable salts of the compound (I) can be prepared by a conventional method, e.g., by treating (I) with a base. Preferred examples of said base are an alkali metal (e.g. sodium, potassium, etc.), an alkaline earth metal (e.g. magnesium, calcium, etc.), the hydroxide or carbonate thereof, alkali metal alkoxide (e.g. sodium methoxide, sodium ethoxide, potassium tert-butoxide, etc.) and the like.

In some case, pharmaceutically acceptable salts of the compound (I) can directly be prepared by reacting a compound (II) with a base.

The starting compound (II) is new and can be prepared by the processes as illustrated in the following reaction schemes.

Process A

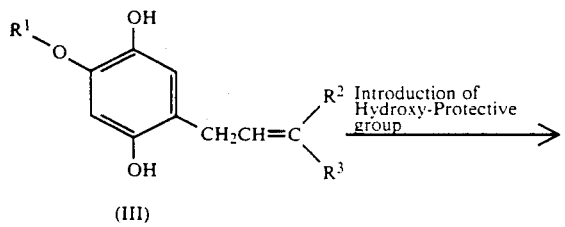

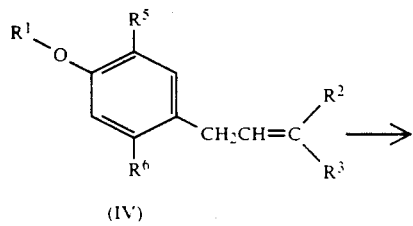

Process B

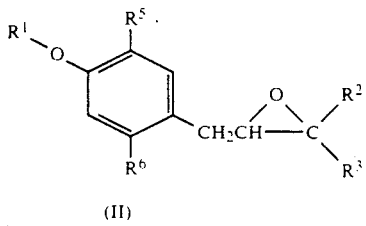

wherein $R^1$, $R^2$, $R^3$, $R^5$ and $R^6$ are each as defined above.

The above-mentioned processes for preparing the starting compound (II) are explained in detail in the following.

Process A

The compound (IV) can be prepared by introducing a hydroxy-protective group into the compound (III).

Suitable introducing agent of the hydroxy-protective group used in this reaction may be acylating agent, which is capable of introducing the acyl group as mentioned before, such as carboxylic acid, carbonic acid, sulfonic acid, carbamic acid and their reactive derivative, for example, an acid halide, an acid anhydride, an activated amide, an activated ester, isocyanate, and the like. Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, trifluoroacetic acid, etc.), aromatic carboxylic acid (e.g. benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), isocyanate, and the like.

This reaction is preferably conducted in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid [e.g. sodium acetate, etc.), trialkylamine (e.g. triethylamine, etc.), pyridine compound (e.g. pyridine, lutidine, picoline, 4-N,N-dimethylaminopyridine, etc.), quinoline, and the like.

In case that the acylating agent is used in a free form or its salt in this reaction, the reaction is preferably conducted in the presence of a conventional condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2methylimidazole), pentamethyleneketene-N-cyclohexylimine, diphenylketene-N-cyclohexylimine, etc.); an olefinic or acetylenic ether compound (e.g. ethoxyacetylene, β-cyclovinylethyl ether), a sulfonic acid ester of N-hydroxybenzotriazole derivative [e.g. 1-(4-chlorobenzenesulfonyloxy)-6-chloro-1H-benzotriazole, etc.], or the like.

The reaction is usually, conducted in a conventional solvent which does not adversely influence the reaction such as dioxane, chloroform, dichloromethane, tetrahydrofuran, pyridine, benzene, N,N-dimethylformamide, etc., and further in case that the base or the introducing agent of the hydroxy-protective group is in liquid, it can be used as a solvent.

The reaction temperature is not critical and the reaction can be carried out under cooling to heating.

Process B

The compound (II) can be prepared by reacting the compound (IV) with an oxidizing agent.

The oxidizing agent to be used in this reaction is a conventional oxidizing agent capable of converting an ethylenic double bond to the corresponding epoxide and may include, as preferred examples, organic peracids and salts thereof, such as perbenzoic acid, o-, m- or p-chloroperbenzoic acid, etc.

This reaction is usually carried out in a solvent which does not adversely influence the reaction such as dichloromethane, acetone, ethyl acetate, chloroform or the like.

The reaction temperature is not critical, and the reaction is usually carried out under cooling to warming.

The compounds obtained by the above processes can be isolated and purified by a conventional method such as pulverization, recrystallization, column chromatography or the like.

The object compound (I) and pharmaceutically acceptable salts thereof possess a strong activity to scavenge reactive oxygen species and organic radicals and are useful for the treatment of the diseases caused by reactive oxygen species and organic radicals in human beings or animals and more particularly are useful for the treatment of ischemic heart diseases (e.g. arrhythmia, coronary vasospasm, necrosis of cardiac tissues, myocardial infarction, etc.), ischemic cerebral diseases (e.g. cerebral infarction, dementia, senile dementia, etc.), disorders of the liver, pancrea and kidney and the like.

In order to illustrate the usefulness of the object compound (I), the pharmacological test data of the compound (I) are shown in the following.

Experiment 1

Inhibitory effect on luminol-induced chemiluminescence (CL) which results from xanthine oxidase-hypoxanthine (XO/HX) reaction.

Method

Four hundred and fifty micro liter of 0.2M hypoxanthine (Kohjin Co., Ltd.) in 0.1M phosphate buffer solution (PBS)(pH 7.6), 10 μl of 1 mg/ml luminol (Nakarai Chemicals, Ltd.) in PBS and 10 μl of sample dissolved in dimethylsulfoxide were mixed in a round-bottomed vial, and preincubated for 3 min. at 37° C. And then, 50 μl of 0.05 unit/ml xanthine oxidase in 0.1M phosphate buffer solution (from cow milk, Boehringer Mannhein GmbH) was added. For the measurement of CL, a Biolumat (LB 9505, Berthold, FRG) was used. The vial containing XO/HX reaction mixture was placed into a Biolumat chamber at 37° C, and CL was continuously monitored using a computer (PC 9801 VM, NEC). Peak intensity was used as an index of CL.

Test Results:

| Compound (No. of Example) | $IC_{50}$ (M) |
|---|---|
| 1 | $3.8 \times 10^{-7}$ |
| 2 | $4.7 \times 10^{-9}$ |
| 3 (FR-901242 substance) | $3.2 \times 10^{-7}$ |

Experiment 2

Inhibitory effect on iron-dependent lipid peroxidation of rat brain homogenate
Method : (reported by J. M. Braughler et al.[1])
1) J. Biol. Chem., 261(22), 10282-10289(1986)

Preparation of rat brain homogenate

Male Sprague-Dawley rat (150 g ~200 g) brain tissue was perfused with Krebs buffer solution composed of 15 mM HEPES*, pH 7.4, 10 mM glucose, 140 mM NaCl, 3.6 mM KCl, 1.5 mM $CaCl_2$, 1.4 mM $KH_2PO_4$, and 0.7 mM $MgCl_2$ via the superior aorta under anesthesia. After decapitation, the brain was quickly removed (minus cerebellum), weighed, and placed in ice-cold Krebs buffer solution. The brain was homogenized in a ratio of 1 g of wet tissue to 9 ml of buffer in a teflon homogenizer. Homogenates were used immediately in lipid p-roxidation assays as follows.
* HEPES : N-(2-hydroxyethyl)piperazine-N'-2-ethanesulfonic acid (Sigma)

Lipid peroxidation

To the reaction mixture consisted of 50 μl of 6.25 mg/ml brain homogenate in Krebs buffer solution, 110 μl of Krebs buffer solution, 20 μl of sample dissolved in methanol was added 20 μl of aqueous 2 mM $Fe(NH_4)_2(SO_4)_2$ solution, which was prepared freshly, at 37° C. After 20 min, the reaction was terminated by the addition of 30 μl of 35% perchloric acid. Then 20 μl of 500 μM desferoxamine mesylate (Sigma) in Krebs buffer solution was added to the reaction mixture to prevent further lipid peroxydation. After centrifugation at 2000 xg, 10 min, 4° C., 50 μl of supernatant was subsequently assayed for lipid peroxide.

Assay of thiobarbituric acid (TBA)-reactive oxidation products

Lipid peroxide was assessed as TBA-reactive product as described by H. Ohkawa et al [2]. The reaction mixture consisted of 50 μl of above-mentioned supernatant, 100 μl of aqueous 8.1% sodium dodecyl sulfate (SDS) solution, 750 μl of aqueous 20% acetic acid solution which was adjusted with aqueous 1N NaOH solution to pH 3.5, 750 μl of aqueous 0.67% 2-thiobarbituric acid solution and 350 μl of distilled water was boiled for 1 hour and cooled in ice bath rapidly. 0.5 ml of distilled water and 2.5 ml of the mixture of n-butanol and pyridine (15:1, V/V) were added, and the mixture was shaken vigorously. After centrifugation at 1250 xg for 10 min, the fluorescence (excitation : 515 nm, emission: 455 nm) of the organic layer was determined.
2) Anal. Biochem., 95, 351-358 (1979)

Test Results:
Inhibition of TBA-reactive products generation (%)

| Concentration (M) | Compound | |
|---|---|---|
| | FR-901242 substance | α-Tocopherol |
| $10^{-7}$ | 11.4 | 0 |
| $10^{-6}$ | 20.0 | 9.3 |
| $10^{-5}$ | 45.4 | 25.7 |
| $10^{-4}$ | 95.5 | 65.3 |

TBA-reactive products generation in the vehicle was 10.3 nmole of TBA-reactive products/mg protein.

The pharmaceutical composition of this invention is provided in various forms such as solid preparations, semi-solid preparations or liquid preparations, which contain the active compound of this invention, i.e., the compound (I) or a pharmaceutically acceptable salt thereof, together with an organic or inorganic carrier or/and excipient suitable for external, oral or parenteral administration. This active component is used in combination with harmless and pharmacologically acceptable auxiliary components to provide such suitable dosage forms as tablets, pellets, capsules, suppositories, solutions, emulsions, suspensions, etc. Examples of such auxiliary components include those which can be effectively utilized in the production of solid, semisolid or liquid preparations, for example, water, glucose, lactose, gelatin, mannitol, starch paste, magnesium trisilicate, corn starch, keratin, colloidal silica, potato starch, urea, etc. Furthermore, such auxiliaries as stabilizers, extenders, colorants and fragrances may also be incorporated. The pharmaceutical compositions according to this invention may also contain preservatives so that the activity of the active component can be preserved. Said compositions should contain the active component in an amount sufficient for the production of desirable therapeutic effects against the progress or actual condition of a disease concerned.

When the pharmaceutical compositions are applied to humans, they are desirably administered by the intravenous, intramuscular or oral route. The effective dose of each active substance depends on the age and/or symptom of the patient to be treated. Generally, however, the pharmaceutical preparations contain about 1 mg, 5mg, 10 mg, 25 mg, 50 mg, 100 mg, 250 mg or 500 mg of the active substance per unit dosage form and are administered to humans or animals at a daily dose of 0.1–100 mg per kilogram of body weight.

The following Preparations and Examples are given for the purpose of illustrating this invention.

Preparation 1

A mixture of 2-methoxy-5-(3-methyl-2-butenyl)hydroquinone (2.35 g) and acetic anhydride (4.6 g) in dry pyridine (20 ml) was stirred for 2 hours at ambient temperature. The mixture was poured into ice water (50 ml) and the separated oil was extracted twice with diethyl ether. The combined extracts were washed twice with diluted hydrochloric acid, dried, and concentrated in vacuo to give a white solid, which was recrystallized from n-hexane to yield 2-methoxy-5-(3-methyl-2-butenyl)hydroquinone diacetate as white crystals (2.89 g).

mp : 75°–77° C.

IR (Nujol) : 1760, 1625, 1515, 1205, 1190 cm$^{-1}$

NMR (CDCl$_3$, δ): 1.68 (3H, s), 1.74 (3H, s), 2.30 (6H, s), 3.13 (2H, d, J=7.5Hz), 3.79 (3H, s), 5.69 (1H, t, J=7.5Hz), 6.65 (1H, s), 6.86 (1H, s)

Preparation 2

To a solution of 2-methoxy-5-(3-methyl-2-butenyl)-hydroquinone diacetate (2.84 g) in dichloromethane (40 ml) was added m-chloroperbenzoic acid (2.09 g, 80% purity) in several portions at 5° C. After the addition, the mixture was stirred for one hour at 5° C., washed twice with a mixture of aqueous sodium bicarbonate solution and aqueous sodium thiosulfinate solution, dried, and concentrated in vacuo. The residue was crystallized from n-hexane to give 5-(2,3-epoxy-3-methylbutyl)-2-methoxyhydroquinone diacetate as a white solid (2.93 g).

mp 93°–96° C.

IR (Nujol) : 1760, 1625, 1515, 1220, 1205 cm$^{-1}$

NMR (CDCl$_3$, δ) : 1.33 (3H, s), 1.37 (3H, s), 2.30 (3H, s), 2.35 (3H, s), 2.69 (2H, dq, J=5Hz and 15Hz), 2.90 (1H, t, J=5Hz), 3.80 (3H, s), 6.69 (1H, s), 6.98 (3H, s)

EXAMPLE 1

To a solution of 5-(2,3-epoxy-3-methylbutyl)-2-methoxyhydroquinone diacetate (1.848 g) in methanol (36 ml) was added potassium hydrogencarbonate (1.50 g) in one portion. The mixture was stirred for 21 hours at ambient temperature and concentrated in vacuo. The residue was dissolved in a mixture of ethyl acetate (30 ml) and saturated sodium chloride solution (30 ml). The separated organic layer was washed with saturated sodium chloride solution, dried, and evaporated to dryness. The oily residue was crystallized from isopropyl ether to yield 2,3-dihydro-2-(1-hydroxy-1-methylethyl)-6-methoxy-5-benzofuranol (964 mg) as a white solid.

mp : 108°–111° C.

NMR CDCl$_3$, δ) 1.20 (3H, s), 1.33 (3H, s , 1.79 (1H, br s), 3.08 (2H, m), 3.83 (3H, s), 4.59 (1H, t, J=10Hz), 5.19 (1H, br s), 6.41 (1H, s), 6.76 (1H, s)

EXAMPLE 2

To a solution of conc. sulfuric acid (1 ml) was added 2,3-dihydro-2-(1-hydroxy-1-methylethyl)-6-methoxy-5-benzofuranol (50 mg) in several portions during a period of few minutes. The mixture was stirred for 10 minutes at ambient temperature and poured into ice water. The separated oil was extracted with methylene chloride. The organic layer was washed with water, dried, and concentrated in vacuo. The residue was purified by column chromatography on silica gel (n-hexane/methylene chloride =1/1) to yield 5-hydroxy-6-methoxy-2-(1-methylethyl)benzofuran (20 mg) as crystals.

mp : 97°–98° C.

NMR (CDCl$_3$, δ) : 1.32 (6H, d, J=8.5Hz), 3.02 (1H, m), 3.95 (3H, s), 5.47 (1H, s), 6.23 (1H, s), 6.99 (2H, s)

EXAMPLE 3

An aqueous seed medium (120 ml) containing 4% of sucrose, 2% of cotton-seed flour, 1% of dried yeast, 1% of polypeptone, 0.2% of potassium dihydrogenphosphate (KH$_2$PO$_4$), 0.2% of calcium carbonate was poured into each of twenty 500 ml Erlenmeyer flasks and sterilized at 121° C. for 30 minutes. A loopful of slant culture of Paecilomyces sp. F-18826 was inoculated to each of the seed medium. The flasks were shaken on a rotary shaker (220 rpm, 5.1 cm throw) at 25° C for 4 days. The resultant seed culture was inoculated to 160 l sterile fermentation medium containing 3% of Pine-Dex (starch acid hydrolysates, Trademark, made by Matsuya Chemical Co.), 1% of glucose, 1% of wheat germ, 0.5% of cotton-seed flour, 2% of potassium dihydrogenphosphate, 1.5% of sodium phosphate, dibasic, 12 water (Na$_2$HPO$_4$·12H$_2$O), 0.001% of zinc sulfate, heptahydrate (ZnSO$_4$·7H$_2$O) and 0.1% of Adekanol (deforming agent, Trademark, made by Asahi Denka Co.) in 160 l stainless steel jar-fermentor. The fermentation was carried out at 25° C for 5 days under aeration of 100 l/min and agitation of 180 rpm.

An amount of FR-901242 substance in the fermentation broth was quantified by measuring the inhibition of luminol oxydation caused by superoxide radical generated from Xanthine Oxidase-Hypoxanthine (XO/HX) system as described in Experiment 1. The sample for the bioassay was prepared as follows; the culture broth was filtered and then extracted with an equal volume of ethyl acetate. The extract was concentrated under reduced pressure to dryness, and was dissolved in an appropriate volume of acetone.

The cultured broth 160 () obtained was filtered with the aid of diatomaseous earth (20 Kg). The filtrate was extracted with 80 l of ethyl acetate. The aqueous layer was reextracted with same volume of ethyl acetate. The extracts were combined and concentrated under reduced pressure to 1.6 l. The condensed extract was dehydrated with 50 g of sulfuric anhydride, and was more concentrated to 0.05 l (46 g). The residue was chromatographed on 2.5 l of silica gel (Kieselgel 60, 70-230 mesh, Merck) using a step gradient with n-hexane-ethyl acetate. The column was washed with 5 l of n-hexne followed by 5 ( of n-hexane-ethyl acetate 10:1, V/V), followed by 5 l of n-hexane-ethyl acetate (4:1, V/V) and the active substance was eluted from the column with 5 ( of n-hexane-ethyl acetate (2:1, V/V). The active fractions were evaporated to dryness under reduced pressure. The residue (4.5 g) was subjected to a column chromatography on 0.6 l of silica gel (Kieselgel 60, 230-400 mesh, Merck) in chloroform-methanol (100:1, V/V) solvent system. The active fractions were evaporated under reduced pressure to give a powder (2.68 g). The powder was dissolved in 35 ml of acetone and then added 400 ml of n-hexane to give 2.16 g of FR-901242 substance as colorless needles.

What we claim is:

1. A compound of the formula :

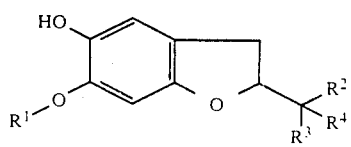
(I)

wherein

R$^1$, R$^2$ and R$^3$ are each lower alkyl

R$^4$ is hydrogen or hydroxy. and a heavy solid line means a single or a double bond, provided that when R$^4$ is hydrogen, then a heavy solid line means a double bond, when R$^4$ is hydroxy, then a heavy solid line means a single bond, or its pharmaceutically acceptable salt.

2. A compound according to claim 1, wherein R$^1$, R$^2$ and R$^3$ are each methyl, R$^4$ is hydroxy and a heavy soiled line means a single bond.

3. A pharmaceutical composition for the treatment of diseases caused by reactive oxygen species and organic radicals comprising a reactive oxygen species and organic radical scavenging effective amount of a compound of claim 1, as an active ingredient, in association with a pharmaceutically acceptable, substantially non-toxic carrier or excipient.

4. A method for therapeutic treatment of the diseases caused by reactive oxygen species and organic radicals which comprise administering a reactive oxygen species and organic radical scavenging effective amount of a compound of claim 1 to human beings or animals in need of such treatment.

* * * * *